US008337909B2

(12) United States Patent
Howard et al.

(10) Patent No.: US 8,337,909 B2
(45) Date of Patent: Dec. 25, 2012

(54) PROCESS OF EXTRACTING PROCYANIDINS BY ALKALINE HYDROLYSIS

(75) Inventors: Luke R. Howard, West Fork, AR (US); Brittany L. White, Fayetteville, AR (US); Ronald L. Prior, Searcy, AR (US)

(73) Assignee: Board of Trustees of the University of Arkansas, Fayetteville, AR (US)

( * ) Notice: Subject to any disclaimer, the term of this patent is extended or adjusted under 35 U.S.C. 154(b) by 294 days.

(21) Appl. No.: 12/794,444

(22) Filed: Jun. 4, 2010

(65) Prior Publication Data

US 2011/0301232 A1 Dec. 8, 2011

(51) Int. Cl.
*A61K 36/00* (2006.01)
*A61K 36/45* (2006.01)
*A61K 36/54* (2006.01)
*A61K 36/87* (2006.01)
*A61K 36/73* (2006.01)
*A61K 36/82* (2006.01)

(52) U.S. Cl. ........ 424/725; 424/732; 424/739; 424/766; 424/729

(58) Field of Classification Search .......... None
See application file for complete search history.

(56) References Cited

U.S. PATENT DOCUMENTS

2008/0199545 A1* 8/2008 Krempin et al. ............. 424/728

FOREIGN PATENT DOCUMENTS

CN 101565414 A * 10/2009

OTHER PUBLICATIONS

Jayaprakasha et al, Antibacterial and antioxidant activities of grape (*Vitis vinifera*) seed extracts. Food research international, 2003. vol. 36, No. 2. p. 117-122.*
Gabetta et al, Characterization of proanthocyanidins from grape seeds. Fitoterapia, (Apr. 2000) vol. 71, No. 2, pp. 162-175.*
Aron, P. M., et al. "Flavan-3-ols: Nature, occurrence and biological activity." Mol. Nutr. Food Res. 2008, 52, 79-104.
Foo, L.Y., et al. "The structure of cranberry proanthocyanidins which inhibit adherence of uropathogenic p-fimbriated *Escherichia coli* in vitro." Phytochem. 2000, 54, 173-181.
Donovan, J. L., et al. "Procyanidins are not bioavailable in rats fed a single meal containing a grape seed extract or the procyanidin B3." Br. J. Nutr. 2002, 87, 299-306.
Holt, R. R., et al. "Procyanidin dimer B2 [epicatechin-(4b-8)-epicatechin] in human plasma after the consumption of a flavanol-rich cocoa." Am. J. Clin. Nut. 2002, 76, 798-804).
Pinelo, M., et al. "Upgrading of grape skins: Significance of plant cell-wall structural components and extraction techniques for phenol release." Trends Food Sci. Tech. 2006, 17, 579-590.
Le Bourvellec, C. "Non-covalent interaction between procyanidins and apple cell wall material: Part I. Effect of some environmental parameters." Biochim. Biophys. Acta. 2004, 1672, 192-202.
Hellstrom, J. K., et al. "HPLC determination of extractable and unextractable proanthocyanidins in plant materials." J. Agric. Food Chem. 2008, 56, 7617-7624.
Madhujith, T., et al. "Antioxidant potential of barley as affected by alkaline hydrolysis and release of insoluble-bound phenolics." Food Chem. 2009, 117, 615-620.
Hellstrom, J. K., et al. "Proanthocyanidins in common food products of plant origin." J. Agric. Food Chem. 2009, 57, 7899-7906.
Arranz, S., et al. "High contents of nonextractable polyphenols in fruits suggest that polyphenol contents of plant foods have been underestimated." J. Agric. Food Chem. 2009, 57, 7298-7303.
Perez-Jimenez, J., et al. "Proanthocyanidin content in foods is largely underestimated in the literature data: An approach to quantification of the missing proanthocyanidins." Food Res. Int. 2009, 42, 1381-1388.
Ossipova, S., et al. "Proanthocyanidins of mountain birch leaves: quantification and properties." Phytochem. Anal. 2001, 12, 128-133.
Matthews, S., et al. "Method for estimation of proanthocyanidins based on their acid depolymerization in the presence of nucleophiles." J. Agric. Food Chem. 1997, 45, 1195-1201.
Hummer, W., et al. "Analysis of proanthocyanidins." Mol. Nutr. Food Res. 2008, 52, 1381-1398.
Adom, K. K., et al. "Antioxidant activity of grains." J. Agric. Food Chem. 2002, 50, 6182-6187; and Barberousse, H., et al. "Analytical methodologies for quantification of ferulic acid and its oligomers." J. Sci. Food Agric. 2008, 88, 1494-1511.
Bocco, A., et al. "Antioxidant activity and phenolic composition of citrus peel and seed extracts." J. Agric. Food Chem. 1998, 46, 2123-2129.
Reed, J. "Cranberry flavonoids, atherosclerosis and cardiovascular health." Crit. Rev. Food Sci. Nutr. 2002, 42, 301-316.
Neto, C. "Cranberry and its phytochemicals: a review of in vitro anticancer studies." J. Nutr. 2007, 137, 186S-193.
Yan, X., et al. "Antioxidant activities and antitumor screening of extracts from cranberry fruit (*Vaccinium macrocarpon*)." J. Agric. Food Chem. 2002, 50, 5844-5849.
Sobota, A. E. "Inhibition of bacterial adherence by cranberry juice: potential use for the treatment of urinary tract infections." J. Urol. 1984, 131, 1013-1016.
Vattem, D.A., et al. "Solid-state production of phenolic antioxidants from cranberry pomace by *Rhizopus oligosporus*." Food Biotech. 2002, 16, 189-210).

(Continued)

*Primary Examiner* — Qiuwen Mi
(74) *Attorney, Agent, or Firm* — Head, Johnson & Kachigian, P.C.

(57) ABSTRACT

A process of extracting procyanidins by alkaline hydrolysis. In particular, a procyanidin-containing material, pomace or residue is treated with an alkali, such as sodium or potassium hydroxide, for a predetermined amount of time and at a predetermined temperature to release procyanidins bound to polysaccharides and/or proteins of the cell wall or depolymerize polymeric procyanidins. After the procyanidins are released by alkaline hydrolysis, the extracts are acidified to obtain a pH level where the procyanidins do not degrade. The process of extracting procyanidins may be utilized to estimate the total amount of bound procyanidins in a plant material, enhance the bioavailability of beneficial procyanidins monomers and/or to treat the residue remaining after conventional solvent extraction for increased procyanidin extraction.

18 Claims, 7 Drawing Sheets

OTHER PUBLICATIONS

Deprez, S., et al. Polymeric proanthocyanidins are catabolized by human colonic microflora into low-molecularweight phenolic acids. J. Nutr. 2000, 130, 2733-2738.

Gu, L., et al. "Screening of foods containing proanthocyanidins and their structural characterization using LC-MS/MS and thiolytic degradation." J. Agric. Food Chem. 2003, 51, 7513-7521.

Kelm, M. A., et al. "High-performance liquid chromatography separation and purification of cacao (*Theobroma cacao* L.) procyanidins according to degree of polymerization using a diol stationary phase." J. Agric. Food Chem. 2006, 54, 1571-1576.

Barberousse, et al. "Analytical methodologies for quantification of ferulic acid and its oligomers." J. Sci Food Agric. 2008, 88, 1494-1511.

\* cited by examiner

PROCESS OF EXTRACTING PROCYANIDINS BY ALKALINE HYDROLYSIS

BACKGROUND OF THE INVENTION

1. Field of the Invention

This invention relates generally to a process of extracting procyanidins by alkaline hydrolysis, and more particularly to a process of extracting procyanidins from procyanidin-containing plant materials, such as cranberry pomace, using alkaline hydrolysis followed by acidification in order to obtain procyanidins in a stable form for use in various applications.

2. Description of the Related Art

Procyanidins are a class of polyphenolic compounds that impart astringency and bitterness to many plant products. In plants, procyanidins are believed to serve as a defense mechanism against potential predators because their bitterness and astringency is undesirable to animals, insects and microbes. (Aron, P. M., et al. "Flavan-3-ols: Nature, occurrence and biological activity." Mol. Nutr. Food Res. 2008, 52, 79-104). Procyanidins are formed via the condensation of the flavan-3-ols catechin and epicatechin and comprise two (2) to several monomeric units. Structurally, the monomeric units may be linked in one of three ways. The "B"-type linkage is the most common and consists of 4β→8 linkage between units. Units connected by both a 2β→O-7 and a 4β→8 are more rigid than 'B'-type linkages and are denoted as "A"-type. The final type of linkage is the "C"-type linkage, which consists of a C-4→C-6 linkage. (Id.). The ability of cranberries to prevent urinary tract infections has been attributed to the presence of procyanidins containing 'A'-type linkages. (Foo, L. Y., et al. "The structure of cranberry proanthocyanidins which inhibit adherence of uropathogenic p-fimbriated *Escherichia coli* in vitro." Phytochem. 2000, 54, 173-181). The bioavailability of procyanidins is dependent upon the size of the molecule, with monomers and dimers being relatively easily absorbed and those larger than trimers being typically poorly absorbed. (Donovan, J. L., et al. "Procyanidins are not bioavailable in rats fed a single meal containing a grape seed extract or the procyanidin B3." *Br. J. Nutr.* 2002, 87, 299-306; and Holt, R. R., et al. "Procyanidin dimer B2 [epicatechin-(4b-8)-epicatechin] in human plasma after the consumption of a flavanol-rich cocoa." *Am. J. Clin. Nutr.* 2002, 76, 798-804).

Polyphenolic compounds, including procyanidins, are commonly perceived to be found mainly in the vacuoles of plants where they are separated from other cellular components. However, many may also be associated with other cellular components, such as the cell wall, especially after cell injury when vacuoles may rupture. This results in the release of phenolic compounds, which may then associate with other cellular components, such as cell wall polysaccharides through hydrogen bonding and hydrophobic interactions. (Pinelo, M., et al. "Upgrading of grape skins: Significance of plant cell-wall structural components and extraction techniques for phenol release." *Trends Food Sci. Tech.* 2006, 17, 579-590). Procyanidins in particular have a strong affinity for cell wall material (Le Bourvellec, C. "Non-covalent interaction between procyanidins and apple cell wall material: Part I. Effect of some environmental parameters." *Biochim. Biophys. Acta.* 2004, 1672, 192-202), with higher molecular weight compounds having a greater affinity for binding than smaller compounds.

The idea of "unextractable" procyanidins has been of great interest because it is believed that the procyanidin contents in plant materials has been underestimated due to the presence of procyanidins bound so tightly to cell wall material that they are not released by conventional extraction methods. (Hellström, J. K., et al. "HPLC determination of extractable and unextractable proanthocyanidins in plant materials." *J. Agric. Food Chem.* 2008, 56, 7617-7624; Madhujith, T., et al. "Antioxidant potential of barley as affected by alkaline hydrolysis and release of insoluble-bound phenolics." *Food Chem.* 2009, 117, 615-620; Hellström, J. K., et al. "Proanthocyanidins in common food products of plant origin." *J. Agric. Food Chem.* 2009, 57, 7899-7906; Arranz, S., et al. "High contents of nonextractable polyphenols in fruits suggest that polyphenol contents of plant foods have been underestimated." *J. Agric. Food Chem.* 2009, 57, 7298-7303; and Perez-Jimenez, J., et al. "Proanthocyanidin content in foods is largely underestimated in the literature data: An approach to quantification of the missing proanthocyanidins." *Food Res. Int.* 2009, 42, 1381-1388). Hellström, et al. ("HPLC determination of extractable and unextractable proanthocyanidins in plant materials." *J. Agric. Food Chem.* 2008, 56, 7617-7624) determined unextractable procyanidins in plant materials by acid-catalyzed depolymerization of the compounds into flavan-3-ols and benzylthioethers using thioacidolysis and determined the amount of unextractable procyanidins in several plant materials including cranberries. (Hellström, J. K., et al. "Proanthocyanidins in common food products of plant origin." *J. Agric. Food Chem.* 2009, 57, 7899-7906). Other researchers have used butanol:HCl with heat to determine the amount of bound procyanidins. (Arranz, S., et al. "High contents of nonextractable polyphenols in fruits suggest that polyphenol contents of plant foods have been underestimated." *J. Agric. Food Chem.* 2009, 57, 7298-7303; and Ossipova, S., et al. "Proanthocyanidins of mountain birch leaves: quantification and properties." *Phytochem. Anal.* 2001, 12, 128-133). The later is based on the principle that under heat and acid, procyanidins are converted to cyanidin, which can be measured spectrophotometrically. Researchers found that apples, peaches and nectarines contain higher levels of nonextractable procyanidins than extractable procyanidins. (Arranz, S., et al. "High contents of nonextractable polyphenols in fruits suggest that polyphenol contents of plant foods have been underestimated." *J. Agric. Food Chem.* 2009, 57, 7298-7303).

The foregoing conventional extraction methods are effective in identifying the presence of bound procyanidins; however, problems exist when using these methods for quantification because of the kinetics of the reactions. Thiolysis yields have been reported to be low (34-63%), and this may be due to impurities, thiolysis resistant bonds or instability of reaction products. (Matthews, S., et al. "Method for estimation of proanthocyanidins based on their acid depolymerization in the presence of nucleophiles." *J. Agric. Food Chem.* 1997, 45, 1195-1201). The butanol:HCl assay produces several side reactions, which result in lower yields, and not all procyanidins react the same under the reaction conditions. (Hummer, W., et al. "Analysis of proanthocyanidins." *Mol. Nutr. Food Res.* 2008, 52, 1381-1398). Additionally, these methods do not preserve the integrity of the procyanidins; therefore, they are unrecoverable. These methods generally use acid and heat to release the procyanidins, and under these conditions, the procyanidins are depolymerized and converted to anthocyanins, such as cyanidin. Cyanidin is an unstable compound and does not have the same biological function as procyanidins, and therefore, while these methods may be an effective means of estimating the amount of bound procyanidins, they are unrecoverable due to the reaction conditions.

Alkaline treatments have been used to extract bound phenolic acids and other phenolic compounds from cereal grains and grasses, such as rice, wheat and corn. The phenolic compounds, namely ferulic acid and p-coumaric acid, are insoluble and bound to cell wall materials where many of the compounds are esterified to cell wall polysaccharides or bound to lignin with ether linkages. Treatment with different concentrations of sodium hydroxide for varying lengths of time has proven to be effective in releasing these bound phenolic compounds from grains. (Adom, K. K., et al. "Antioxidant activity of grains." *J. Agric. Food Chem.* 2002, 50, 6182-6187; and Barberousse, H., et al. "Analytical methodologies for quantification of ferulic acid and its oligomers." *J. Sci. Food Agric.* 2008, 88, 1494-1511). Alkaline hydrolysis has also been used to effectively extract bound ferulic, p-coumaric, caffeic and sinapic acids from citrus peel and seeds. (Bocco, A., et al. "Antioxidant activity and phenolic composition of citrus peel and seed extracts." *J. Agric. Food Chem.* 1998, 46, 2123-2129). In fruits, however, conventional extraction methods do not utilize an alkaline treatment to release bound phenolic compounds because many phenolic compounds in fruits, including anthocyanins, are unstable in alkaline conditions. Additionally, harsh processing conditions such as alkaline hydrolysis may result in depolymerization of polymeric procyanidins to release lower molecular weight procyanidins such as monomers and dimers. This phenomenon may be difficult to distinguish from enhanced extraction, but may play an important role in the apparent increased extraction of procyanidins.

Cranberries (*Vaccinium macrocarpon*) are growing in popularity due to the increasing information regarding their health benefits. Cranberry juice has long been recognized for its ability to prevent urinary tract infections. In addition, there are several other health benefits associated with cranberries, including antioxidant, antitumor, antiulcer, anti-inflammatory and antiatherosclerotic activities. (Reed, J. "Cranberry flavonoids, atherosclerosis and cardiovascular health." *Crit. Rev. Food Sci. Nutr.* 2002, 42, 301-316; Neto, C. "Cranberry and its phytochemicals: a review of in vitro anticancer studies." *J. Nutr.* 2007, 137, 186S-193; Yan, X., et al. "Antioxidant activities and antitumor screening of extracts from cranberry fruit (*Vaccinium macrocarpon*)." *J. Agric. Food Chem.* 2002, 50, 5844-5849; and Sobota, A. E. "Inhibition of bacterial adherence by cranberry juice: potential use for the treatment of urinary tract infections." *J. Urol.* 1984, 131, 1013-1016).

Cranberry pomace is composed primarily of seeds, skins and stems, which are leftover from the juicing and canning processes of the cranberry processing industry. (Vattem, D. A., et al. "Solid-state production of phenolic antioxidants from cranberry pomace by *Rhizopus oligosporus*." *Food Biotech.* 2002, 16, 189-210). The seeds and skins of cranberries are a rich source of polyphenolic compounds, which have shown to be responsible for the numerous health benefits associated with the cranberries.

In addition to cranberries, many other types of plant materials are known to contain procyanidins, such as apples, pine bark, cinnamon, cocoa, grapes, bilberry, black currant, green tea, black tea, chokeberry, blueberry and sorghum.

It is therefore desirable to provide a process of using alkaline hydrolysis to extract procyanidins, which are not extracted by conventional extraction methods.

It is further desirable to provide a process of extracting procyanidins from procyanidin-containing plant materials using alkaline hydrolysis followed by acidification in order to release the procyanidins in a stable form.

It is still further desirable to provide a process of extracting bound procyanidins by alkaline hydrolysis that may be utilized to estimate the amount of bound or unextractable procyanidins in procyanidin-containing plant materials.

It is yet further desirable to provide a process of extracting procyanidins by alkaline hydrolysis that may be utilized industrially as a process of recovering procyanidins from procyanidin-containing plant materials, which may subsequently be used in dietary supplements or added to products to enhance health benefits, for example, protection against urinary tract infections.

It is yet further desirable to provide a process of extracting procyanidins by alkaline hydrolysis that enhances the bioavailability of procyanidin oligomers, namely monomeric, dimeric and trimeric procyanidins.

It is yet further desirable to provide a process of extracting procyanidins by alkaline hydrolysis capable of separating low molecular weight procyanidins (monomers, dimers and trimers) from high molecular weight procyanidins.

It is still yet further desirable to provide a process of extracting procyanidins by alkaline hydrolysis that may be utilized on a resulting residue from conventional extraction methods in order to increase the procyanidin extraction yield.

SUMMARY OF THE INVENTION

In general, in a first aspect, the invention relates to a process of extracting procyanidins from a procyanidin-containing plant material. The process includes the steps of treating the pomace with a strong alkali for a predetermined amount of time and at a predetermined temperature; then, adjusting the pH of the pomace in a manner effective to prevent the procyanidins in the pomace from degrading; and then, extracting the procyanidins from the pomace. The material may be any plant material that contains procyanidins, such as cranberry pomace, apple pomace, pine bark, cinnamon, cocoa, grape pomace, grape seeds, bilberry pomace, black currant pomace, green tea, black tea, chokeberry pomace, blueberry pomace or sorghum.

The strong alkali and the procyanidin-containing material may be mixed at a ratio of approximately 2:1 to approximately 10:1, and the strong alkali utilized for the alkaline hydrolysis may be sodium or potassium hydroxide having a normality of approximately 0.1 to approximately 6.0. The predetermined amount of time of the process may range from approximately five (5) minutes up to approximately twenty-four (24) hours, while the predetermined temperature may range from approximately 25° C. to approximately 60° C. Further, the step adjusting the pH can include adjusting the pH to approximately two (2) to approximately seven (7) using an acid, such as concentrated hydrochloric acid having a normality of approximately four (4). In addition, the process may include extracting lipids by shaking with hexane after adjusting the pH and before extracting the procyanidins.

Extracting the procyanidins under the process can include extracting procyanidins from the pomace using ethyl acetate, extracting procyanidins by homogenization with acetone:water:acetic acid, and/or extracting procyanidin monomers, dimers and trimers from the pomace with ethyl acetate and extracting procyanidin tetramers, pentamers and hexamers from the pomace by homogenization with acetone:water:acetic acid.

In particular, the process may include treating a pomace with a hydroxide compound having a normality of approximately 0.1 to approximately 6.0 in the presence of an inert gas such as nitrogen or argon, for approximately fifteen (15) minutes and at a temperature of approximately 60° C.; then, neutralizing the sodium hydroxide to a pH of approximately two (2) to approximately seven (7); then, extracting lipids from the cranberry pomace using hexane; then, extracting procyanidin monomers, dimers and trimers from the cranberry pomace using ethyl acetate; and then, extracting procyanidin tetramers, pentamers and hexamers from the cranberry pomace by homogenization with acetone:water:acetic acid.

In general, in a second aspect, the invention relates to a process of extracting procyanidins from a procyanidin-containing pomace residue by homogenizing a procyanidin-containing pomace and a solvent to form a pomace mixture; then, extracting procyanidins monomers through polymers from the pomace mixture leaving the pomace residue; then, removing any excess of the solvent from the pomace residue; then, dissolving the pomace residue in an aqueous solution of a hydroxide compound; then, heating the aqueous solution to a predetermined temperature for a predetermined amount of time, such as to a temperature of approximately 25° C. to approximately 60° C. for approximately five (5) minutes to approximately twenty-four (24) hours; then, substantially neutralizing the pH of the aqueous solution using an acid; and then, extracting the procyanidins from the pomace residue.

The process of extracting procyanidins from the procyanidin-containing pomace residue may further include cooling the aqueous solution after heating and before substantially neutralizing the pH of the aqueous solution. The process can also include separating lipids in the aqueous solution by shaking with hexane after substantially neutralizing the pH of the aqueous solution and before extracting the procyanidins.

Under the process, the solvent may be acetone:water:acetic acid having a volumetric ratio of approximately 70:29.5:0.5, and the hydroxide compound may be sodium or potassium hydroxide having a normality from approximately 0.1 to approximately 6.0. Further, the step of dissolving the pomace residue in the aqueous solution of the hydroxide compound may include mixing the hydroxide compound and the pomace at a ratio of approximately 2:1 to approximately 10:1. In addition, the step of substantially neutralizing the pH of the aqueous solution may further include adjusting the pH of the aqueous solution to a pH of between about two (2) and about seven (7) using concentrated hydrochloric acid having a normality of approximately four (4). Furthermore, the step of extracting the procyanidins can include extracting procyanidin monomers, dimers and trimers from the pomace residue with ethyl acetate and extracting procyanidin tetramers, pentamers and hexamers from the pomace residue by homogenization with acetone:water:acetic acid.

Figure 1:
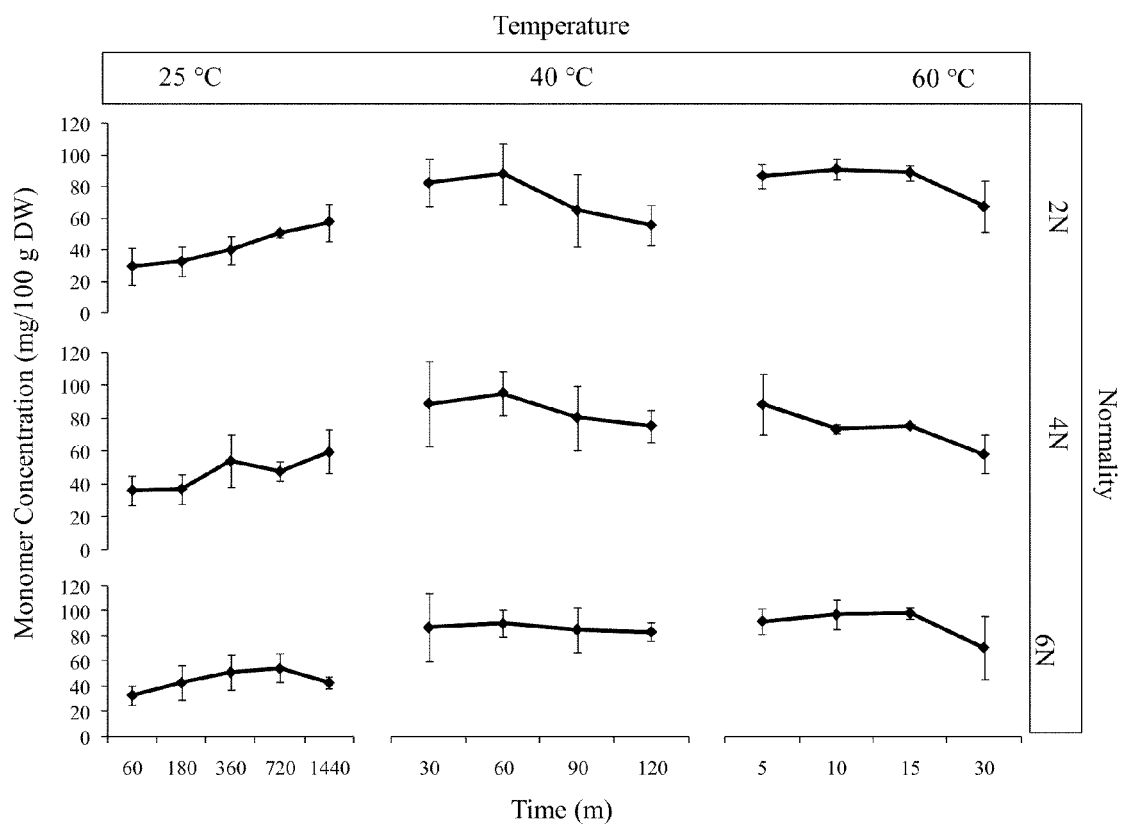
FIG. 1 is a graphical illustration of changes in procyanidin monomer (DP1) compositions of cranberry pomace treated with different concentrations of sodium hydroxide at different temperatures for varying amounts of time in accordance with an illustrative embodiment of the process of extracting bound procyanidins by alkaline hydrolysis disclosed herein.

Other advantages and features will be apparent from the following description and from the claims.

DETAILED DESCRIPTION OF THE INVENTION

The processes discussed herein are merely illustrative of specific manners in which to make and use this invention and are not to be interpreted as limiting in scope.

While the processes have been described with a certain degree of particularity, it is to be noted that many modifications may be made in the construction and the arrangement of the function details disclosed herein without departing from the spirit and scope of this disclosure. It is understood that the processes are not limited to the embodiments set forth herein for purposes of exemplification.

A process of extracting procyanidins by alkaline hydrolysis whereby a procyanidin-containing material, pomace or residue is treated with an alkali, such as sodium or potassium hydroxide, for a predetermined amount of time and at a predetermined temperature to release procyanidins bound to polysaccharides and/or proteins of the cell wall, the pomace or the residue, as the case may be, or to depolymerize polymeric procyanidins to release lower molecular weight procyanidins. After the procyanidins are released by alkaline hydrolysis, the extracts are acidified to obtain a pH level where the extracted procyanidins do not degrade.

The process of extracting procyanidins by alkaline hydrolysis releases procyanidins or depolymerizes polymeric procyanidins, which may subsequently be recovered to be used in various applications. For example, the process of extracting procyanidins may be utilized to estimate the total amount of procyanidins in many plant materials, thus giving a more accurate estimate of the total procyanidins in the procyanidin-containing plant material since, although they are unextractable, they may still be biologically important. Secondly, the process of extracting procyanidins by alkaline hydrolysis could enhance the bioavailability of the procyanidin compounds. As fully discussed below, DP1 and DP2 procyanidins are released in the greatest quantities compared to other oligomers when the process of extracting procyanidins is used, which is important because DP1, DP2, and to a lesser extent DP3 procyanidins are absorbed by the human body, whereas higher oligomers and polymers are not. The larger oligomers and polymers, however, may still confer health benefits due to their ability to be metabolized by colonic microflora, which in turn produce smaller molecules, such as phenolic acids that may subsequently be absorbed. (Deprez, S., et al. Polymeric proanthocyanidins are catabolized by human colonic microflora into low-molecular-weight phenolic acids." *J. Nutr.* 2000, 130, 2733-2738). Additionally, free procyanidins may be more available for microbial metabolism than those bound within the cell wall. Lastly, the process of extracting procyanidins by alkaline hydrolysis could be used industrially as a process of recovering procyanidins from a procyanidin-containing material. Polyphenolics are often recovered from waste materials to be used in dietary supplements or fortification purposes. After anthocyanins, flavonols, and other phenolics have been extracted, the residue can be treated with an alkali, neutralized, and desalted. The released procyanidins are then extracted and may be used in a variety of applications.

The process of extracting procyanidins by alkaline hydrolysis may be utilized on any procyanidin-containing plant material, such as a fruit, pomace or residue. For example, the procyanidin-containing plant material may be cranberry, apple, pine bark, cinnamon, cocoa, grape, grape seed, bilberry, black currant, green tea, black tea, chokeberry, blueberry or sorghum. The process includes treating the procyanidin-containing plant material with a strong alkali, such as sodium or potassium hydroxide, for a predetermined amount of time, such as approximately five (5) minutes to approximately twenty-four (24) hours, and at a predetermined temperature, such as approximately 25° C. to approximately 60° C. After treatment with the alkali, the pH is adjusted in a manner effective to prevent the procyanidins in the procyanidin-containing plant material from degrading, such as to a pH of approximately two (2) to approximately seven (7). The lipids may be extracted after the pH is adjusted, and then the procyanidins are extracted from the procyanidin-containing plant material. For example, the procyanidins monomers, dimers and trimers can be extracted using ethyl acetate and the procyanidin tetramers, pentamers and hexamers can be extracted by homogenization with a solvent, such as acetone:water:acetic acid.

When the process is utilized to extract procyanidins from a procyanidin-containing pomace residue, a procyanidin-containing pomace and a solvent are homogenized to form a pomace mixture, at which point procyanidins monomers through polymers can be extracted from the pomace mixture leaving a pomace residue. Any excess solvent can then be removed from the pomace residue, at which point the pomace residue is treated with in an aqueous solution of a hydroxide compound, namely sodium or potassium hydroxide, in the presence of an inert gas, such as nitrogen or argon, to avoid the oxidation of phenolic compounds. The aqueous solution is then heated to a predetermined temperature for a predetermined amount of time, such as to a temperature of approximately 25° C. to approximately 60° C. for approximately five (5) minutes to approximately twenty-four (24) hours. The aqueous solution can then be cooled and the pH is substantially neutralized using a suitable acid to a pH of approximately two (2) to approximately seven (7). After substantially neutralizing the pH of the aqueous solution so that the procyanidins do not degrade, the lipids may be separated and extracted from the pomace residue, and at this point in the process, the procyanidins may be extracted from the pomace residue.

When the process is utilized to extract procyanidins of a procyanidin-containing material in order to estimate of the total procyanidins, the procyanidin-containing material is treated with a hydroxide compound in the presence of an inert gas for approximately five (5) minutes to approximately twenty-four (24) hours and at a temperature of approximately 25° C. to approximately 60° C. to extract the procyanidins of the procyanidin-containing material. The pH can then be substantially neutralized in a manner effective to prevent the procyanidins from degrading, such as by using a mineral acid. The procyanidins can then be extracted from the material using a solvent.

The solvent used in the process of extracting bound procyanidins by alkaline hydrolysis can be any food grade organic solvent, which will solubilize the procyanidin monomers, oligomers and polymers present in the procyanidin-containing plant materials. For example, the solvent may be chosen from the group consisting of lower alcohols, such as methanol, ethanol and isopropanol or ethyl acetate and acetone. The solvents can be used in either aqueous solution or undiluted.

The acid used in the process of extracting bound procyanidins by alkaline hydrolysis can be a mineral acid, such as concentrated hydrochloric acid, or a food grade non-mineral acid, such as formic acid or acetic acid.

Test Procedures

In the examples which follow, the process of extracting bound procyanidins by alkaline hydrolysis was used to extract procyanidins from a procyanidin-containing material, namely cranberry pomace, grape seeds, blueberry pomace and grape pomace, or to depolymerize polymeric procyanidins to release lower molecular weight procyanidins. In Examples 1 and 2, five (5) milliliters (mL) of sodium hydroxide (2, 4, or 6N) was added to 0.5 grams of cranberry pomace in screw top glass tubes, and the tubes were flushed with an inert gas, such as nitrogen or argon, to avoid the oxidation of phenolic compounds. The tubes were then placed into a water bath set at 25, 40, or 60° C. with shaking for varying amounts of time, which depended on the temperature. In Example 3, 0.5 grams of cranberry pomace was treated with varying concentrations of sodium hydroxide (0.1, 0.275, 0.05, 1.0, 2.0, 4.0 and 6.0N) at 60° C. for fifteen (15) minutes. In Example 4, cranberry pomace was treated with 2N sodium hydroxide at 60° C. for fifteen (15) minutes. In Example 5, blueberry and grape pomace and three (3) varieties of wine grape seeds were treated with 2N sodium hydroxide for fifteen (15) minutes, while in Example 6, alkaline hydrolysis was performed using 2N potassium hydroxide at 60° C. for fifteen (15) minutes in order to release procyanidins from procyanidin-containing plant materials. The alkali, hydroxide compound was then neutralized to a pH of about two (2) to about seven (7) with concentrated hydrochloric acid. Procyanidins were extracted with a solvent and analyzed using normal phase high performance liquid chromatography (HPLC).

Dried cranberry pomace (Decas Cranberry Company, Carver, Mass.) was ground to pass through a 1000 μm sieve screen using an Udy Cyclone Sample Mill (Fort Collins, Colo.) and stored at −70° C.

Alkaline treatment of cranberry pomace. The ground cranberry pomace (0.5 g) was weighed and placed into glass, screw-top tubes. Five (5) mL of 2N, 4N, or 6N sodium hydroxide (Fisher Scientific, Pittsburgh, Pa.) was added to the tubes, which were then flushed with nitrogen for thirty (30) seconds, capped, and vortexed. The tubes were then placed in a shaking water bath (200 rpm) set at 25, 40, or 60° C. for five (5) minutes to twenty-four (24) hours depending on the temperature. After tubes were removed from the water bath, they were placed in an ice bath, and their pH was adjusted to about two (2) to about seven (7) using 4N hydrochloric acid.

Alkaline treatment of residue following conventional solvent extraction. The dried cranberry pomace (0.5 g) was extracted using the homogenization method described below. After three extractions, the residue was collected, and the excess acetone was removed using a SpeedVac® concentrator (ThermoSavant, Holbrook, N.Y.). The residue was then alkaline treated using five (5) mL of 2N sodium hydroxide for fifteen (15) minutes at 60° C. The pH was adjusted to about two (2) to about seven (7) using 4N hydrochloric acid, and procyanidins were extracted as described below.

Extraction of procyanidins. Neutralized samples from the alkaline treatment of pomace were transferred to 250 mL plastic bottles. Lipids were extracted by shaking with forty (40) mL hexane and centrifuging for ten (10) minutes at 10,864×g, and the lipid fraction was discarded. Procyanidin monomers, dimers, and trimers were extracted with forty (40) mL of ethyl acetate (EMD Biosciences, Madison, Wis.) and centrifuged for ten (10) minutes at 10,864×g. Ethyl acetate extraction was repeated, and the extracts were pooled.

Extraction of procyanidin monomers through polymers was performed using a T18 Basic Ultra-Turrax® homogenizer (IKA WORKS, Wilmington, N.C., USA). Neutralized samples were mixed with twenty (20) mL of acetone:water:acetic acid (70:29.5:0.5 v/v/v) (EMD Biosciences, Madison, Wis.), homogenized for one (1) minute, and filtered through Miracloth. The extraction was repeated two (2) more times, the extracts pooled, and volume adjusted to 100 mL with extraction solvent.

Extraction with ethyl acetate allows for quantification of monomers, dimers, and trimers and provides a quick process to screen extraction conditions. Higher oligomers and polymers were extracted using homogenization with acetone:water:acetic acid which extracts procyanidin monomers through polymers (DP≧10).

Sephadex LH-20 isolation of procyanidins. Procyanidins extracted using acetone:water:acetic acid were isolated from sugars and other phenolic compounds by solid phase extraction using Sephadex LH-20 (Sigma Chemical Co., St. Louis, Mo.) according to the method described by Gu, L., et al. "Screening of foods containing proanthocyanidins and their structural characterization using LC-MS/MS and thiolytic degradation." *J. Agric. Food Chem.* 2003, 51, 7513-7521.

HPLC analysis of procyanidins. Ethyl acetate extracts and extracts resulting from LH-20 isolation were evaporated to dryness using a SpeedVac® concentrator, re-suspended in two (2) mL AWA and filtered through 0.45 µm filters for HPLC analysis. Procyanidins were separated using the method described by Kelm, M. A., et al. "High-performance liquid chromatography separation and purification of cacao (*Theobroma cacao* L.) procyanidins according to degree of polymerization using a diol stationary phase." *J. Agric. Food Chem.* 2006, 54, 1571-1576, with modifications. Procyanidins were quantified using a mixture of standards (DP1-DP10) (Masterfoods Inc., Hackettstown, N.J.) isolated from cocoa. (Id.). A-type procyanidins were quantified as B-type equivalents.

Experimental design and analysis. A split-plot randomized block design was used for treatment application with water bath temperature as the whole plot in a randomized complete block design with three blocks. Sodium hydroxide concentration was the split plot. Time was nested within temperature, which is denoted as time [temperature]. A single treatment consisted of one temperature, one time, and one sodium hydroxide concentration. Three water bath temperatures (25, 40, 60° C.) and three sodium hydroxide concentrations (2, 4, and 6N) were evaluated. Time of treatment varied depending on temperature. There were a total of thirty-nine 39 treatments, and levels of each factor were randomized within each plot, as illustrated in Table 1 below.

TABLE 1

Treatment Conditions for Alkaline Hydrolysis

| Temperature (° C.) | Time | Concentration (N) |
|---|---|---|
| 25 | 1 h | 2, 4, 6 |
|  | 3 h | 2, 4, 6 |
|  | 6 h | 2, 4, 6 |
|  | 12 h | 2, 4, 6 |
|  | 24 h | 2, 4, 6 |
| 40 | 30 m | 2, 4, 6 |
|  | 1 h | 2, 4, 6 |
|  | 1.5 h | 2, 4, 6 |
|  | 2 h | 2, 4, 6 |
| 60 | 5 m | 2, 4, 6 |
|  | 10 m | 2, 4, 6 |
|  | 15 m | 2, 4, 6 |
|  | 30 m | 2, 4, 6 |

Analysis of variance and mean separations were determined by the PROC MIXED procedure using SAS (SAS.9.1, SAS Institute, Cary, N.C.). Differences between means were determined using the protected LSD ($\alpha=0.05$).

Example 1

Cranberry pomace was treated with varying concentrations of sodium hydroxide at different temperatures for different amounts of time. Monomeric (DP1), dimeric (DP2), and trimeric (DP3) procyanidins were extracted from the alkaline treated pomace. The overall analysis of variance is presented in Table 2.

TABLE 2

Analysis of Variance for Procyanidin Extraction Using Sodium Hydroxide

| Source | df | F-value | P |
|---|---|---|---|
| Monomer | | | |
| temperature | 2 | 89.38 | <0.0001 |
| time [temperature] | 10 | 3.59 | 0.0050 |
| normality | 2 | 1.13 | 0.3292 |
| normality × temperature | 4 | 0.81 | 0.5270 |
| normality × time [temperature] | 20 | 1.88 | 0.0351 |
| Dimer | | | |
| temperature | 2 | 67.59 | <0.0001 |
| time [temperature] | 10 | 5.70 | 0.0002 |
| normality | 2 | 2.75 | 0.0731 |
| normality × temperature | 4 | 0.93 | 0.4564 |
| normality × time [temperature] | 20 | 2.11 | 0.0160 |
| Trimer | | | |
| temperature | 2 | 20.37 | <0.0001 |
| time [temperature] | 10 | 3.74 | 0.0039 |
| normality | 2 | 0.69 | 0.5054 |
| normality × temperature | 4 | 0.42 | 0.7910 |
| normality × time [temperature] | 20 | 1.78 | 0.0489 |

As can be seen from Table 3 below, when averaged over all normalities and times, the effect of temperature was significant for DP1-DP3 procyanidins.

TABLE 3

Procyanidin (DP1-DP3) Concentration (mg/100 g DW) of Cranberry Pomace Treated with Sodium Hydroxide at Different Temperatures.

| Temperature (° C.) | DP1 | DP2 | DP3 |
|---|---|---|---|
| 25 | 44.6 ± 1.9b[a,b] | 248.9 ± 12.8c | 85.6 ± 4.5c |
| 40 | 84.8 ± 3.1a | 420.3 ± 11.8b | 114.7 ± 4.3b |
| 60 | 85.5 ± 2.6a | 519.3 ± 22.4a | 144.5 ± 9.2a |

[a]Values represent means ± standard error
[b]Values within each column followed by the same letters are not significantly different (p > 0.05)

As can be seen, monomers were extracted better at 40° C. and 60° C. than at 25° C. Dimers and trimers were extracted best at 60° C., followed by 40° C. and 25° C. Generally, higher temperatures facilitated increased extraction of procyanidins.

The highest order reaction which showed significance for DP1-DP3 procyanidins was normality×time [temperature]. The significance of this interaction indicates that extractability of procyanidins at certain time/temperature combinations is different depending on the normality of sodium hydroxide used. Comparisons were made among all time/temperature/normality combinations. The effects of temperature and normality over time for DP1 extraction is presented in FIG. 1. As can be seen, DP1 extraction generally increased up to the maximum time (twenty-four (24) hours) for pomace treated at 25° C. with 2N and 4N sodium hydroxide; however, extraction decreased at twelve (12) hours using 6N sodium hydroxide. At 40° C. with 2N sodium hydroxide, extraction decreased after sixty (60) minutes for all concentrations of sodium hydroxide; however, there was no difference over time for 40° C. with 4N and 6N sodium hydroxide. At 60° C. with all concentrations of sodium hydroxide, extraction of monomers remained the same up to fifteen (15) minutes and decreased after thirty (30) minutes. Several conditions yielded the highest amount of monomers (DP1), and all of the conditions were at either 40° C. or 60° C.

Figure 2:
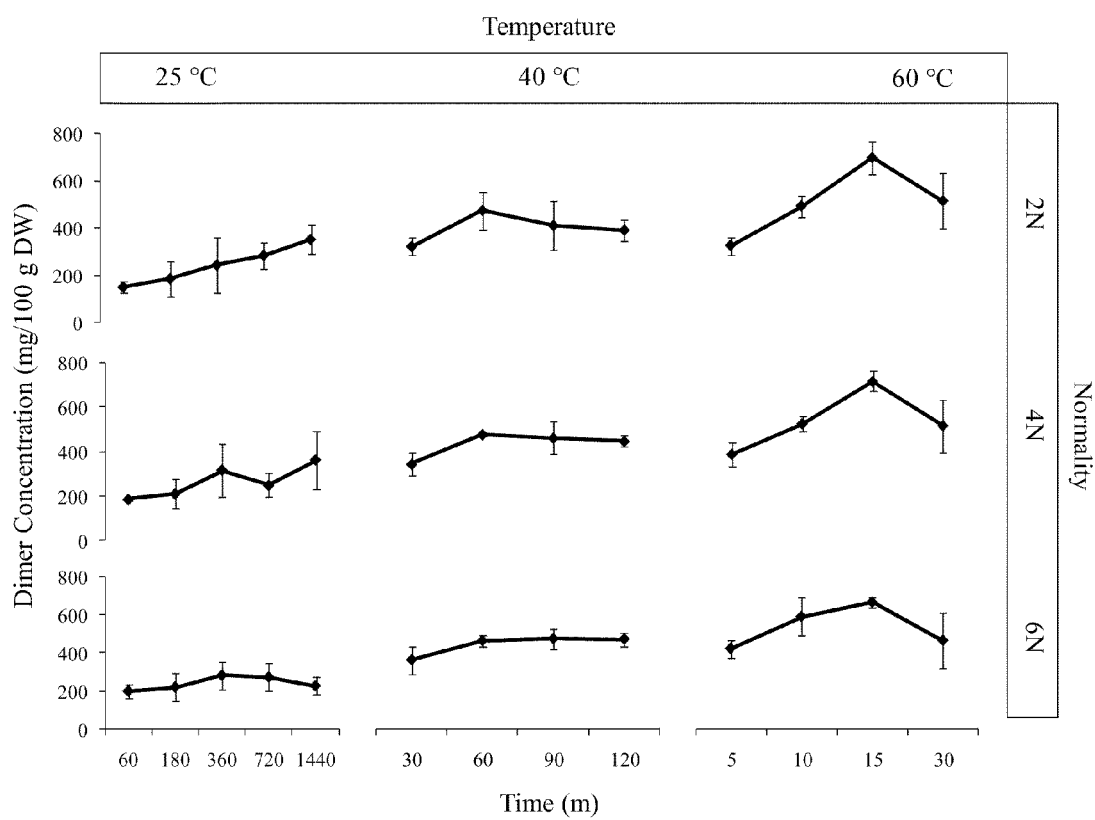
FIG. 2 is a graphical illustration of changes in procyanidin dimer (DP2) compositions of cranberry pomace treated with different concentrations of sodium hydroxide at different temperatures for varying amounts of time in accordance with an illustrative embodiment of the process of extracting procyanidins by alkaline hydrolysis disclosed herein.

The effects of temperature and normality over time for DP2 extraction is presented in FIG. 2. Similar to DP1 extraction, DP2 extraction at 25° C. increased up to twenty-four (24) hours when treated with 2N and 4N sodium hydroxide, but there was no difference over time with 6N sodium hydroxide at 25° C. At 40° C. with 2N and 4N sodium hydroxide, extraction increased at sixty (60) minutes, then leveled off. However, there was no difference over time when 6N sodium hydroxide was used. At 60° C. with 2N and 4N N sodium hydroxide, extraction increased after ten (10) minutes and again after fifteen (15) minutes, and then decreased after thirty (30) minutes. Using 6N sodium hydroxide, extraction also increased after ten (10) minutes, remained the same after fifteen (15) minutes, and decreased after thirty (30) minutes. Overall, dimer (DP2) extraction was greatest at 60° C. for fifteen (15) minutes using all three concentrations of sodium hydroxide.

Figure 3:
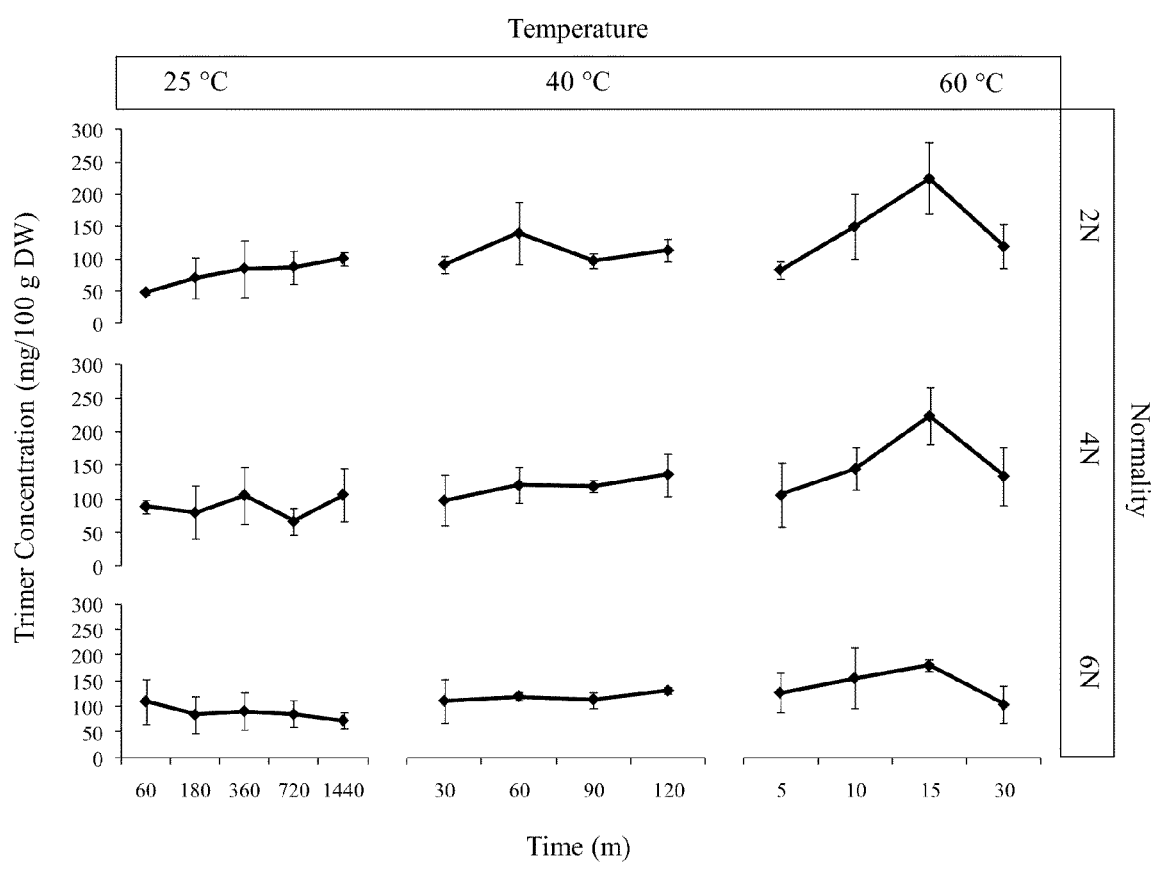
FIG. 3 is a graphical illustration of changes in procyanidin trimer (DP3) compositions of cranberry pomace treated with different concentrations of sodium hydroxide at different temperatures for varying amounts of time in accordance with an illustrative embodiment of the process of extracting procyanidins by alkaline hydrolysis disclosed herein.

The effects of temperature and normality over time for DP3 extraction is presented in FIG. 3. At 25° C. with 2N sodium hydroxide, there were more DP3 procyanidins extracted after twenty-four (24) hours than after only one (1) hour. For those treated with 4N and 6N sodium hydroxide at 25° C., there were no differences among treatment times. There were also no differences among any treatment times or normalities within samples treated at 40° C. At 60° C., however, extraction increased after ten (10) minutes and again after fifteen (15) minutes and then decreased after thirty (30) minutes when 2N sodium hydroxide was used. Using 4N and 6N sodium hydroxide, extraction increased only after fifteen (15) minutes and then decreased after thirty (30) minutes. When comparing all conditions, trimer (DP3) extraction was greatest at 60° C. for fifteen (15) minutes using 2N and 4N sodium hydroxide.

Treatment of cranberry pomace with sodium hydroxide using the aforementioned conditions was compared to the conventional extraction method of homogenization with acetone:water:acetic acid. Procyanidin monomers through hexamers were extracted, and these results are presented in FIG. 4. HPLC chromatograms of procyanidins in cranberry pomace before and after treatment with sodium hydroxide are presented in FIGS. 5A and 5B. The procyanidins in the pomace were previously identified by LC-MS and MALDI-TOF-MS. (White, B. L., et al. "Proximate and polyphenolic characterization of cranberry pomace." *J. Agric. Food Chem.* DOI:10.1021/jf902829g). As can be seen, procyanidin monomers (DP1) and oligomers (DP2-DP6) were better extracted after treatment with sodium hydroxide. The increase in extraction was most evident in DP1 (14.9-fold) and DP2 (11.4-fold) procyanidins. In total, treatment with sodium hydroxide resulted in a 9.4-fold increase in extraction of procyanidin monomers and oligomers. Homogenization with acetone:water:acetic acid also allowed for extraction of polymeric procyanidins (DP≧10). There was a reduction in polymeric procyanidins in pomace treated with sodium hydroxide (4064.8 mg/100 g DW) compared to conventional solvent extraction (14026.9 mg/100 g DW).

Example 2

Anthocyanins, flavonols, and "free" procyanidins were extracted from cranberry pomace by homogenization with acetone:water:acetic acid, and the resulting residue was collected and treated with 2N sodium hydroxide at 60° C. for fifteen (15) minutes. Table 4 below shows the quantities of anthocyanins, flavonols and procyanidins extracted from the cranberry pomace by conventional solvent extraction.

TABLE 4

Composition and Content of Polyphenolics Extracted from Cranberry Pomace by Homogenization with Conventional Solvent[a]

| Polyphenolic Compound | Concentration (mg/100 g DW) |
|---|---|
| Anthocyanins | |
| cyanidin 3-galactoside | 13.1 ± 1.0[b] |
| cyanidin 3-glucoside | 6.3 ± 0.2 |
| cyanidin 3-arabinoside | 35.9 ± 3.9 |
| peonidin 3-galactoside | 17.6 ± 1.9 |
| peonidin 3-glucoside | 9.5 ± 0.4 |
| peonidin 3-arabinoside | 20.7 ± 3.0 |
| total | 103.1 ± 10.4 |
| Flavonols[c] | |
| myricetin 3-xyloside | 1.4 ± 0.1 |
| myricetin 3-arabinoside | 1.6 ± 0.2 |
| quercetin 3-galactoside | 2.6 ± 0.2 |
| quercetin 3-xyloside | 5.7 ± 0.4 |
| quercetin 3-arabinopyranoside | 4.7 ± 0.3 |
| quercetin 3-arabinofuranoside | 6.5 ± 0.2 |
| quercetin 3-rhamnoside | 9.6 ± 0.2 |
| myricetin | 57.2 ± 1.3 |
| methoxyquercetin 3-xyloside | 1.9 ± 0.2 |
| quercetin 3-coumaroyl galactoside | 0.7 ± 0.1 |
| unidentified | 6.9 ± 0.2 |
| quercetin | 220.8 ± 3.0 |
| quercetin 3-benzoyl galactoside | 18.3 ± 0.5 |
| Total | 348.9 ± 4.7 |

TABLE 4-continued

Composition and Content of Polyphenolics Extracted from
Cranberry Pomace by Homogenization with Conventional Solvent[a]

| Polyphenolic Compound | Concentration (mg/100 g DW) |
|---|---|
| Procyanidins[d] | |
| monomer (DP1) | 5.8 ± 0.4 |
| dimer (DP2A) | 82.6 ± 2.3 |
| dimer (DP2B) | 4.4 ± 0.8 |
| trimer (DP3A) | 30.8 ± 2.5 |
| tetramer (DP4B) | 22.9 ± 3.6 |
| pentamer (DP5A) | 7.1 ± 1.2 |
| hexamer (DP6A) | 21.1 ± 1.3 |
| total oligomers | 167.3 ± 5.9 |
| polymer (DP ≧ 10) | 14026.9 ± 1940.1 |

Figure 4:
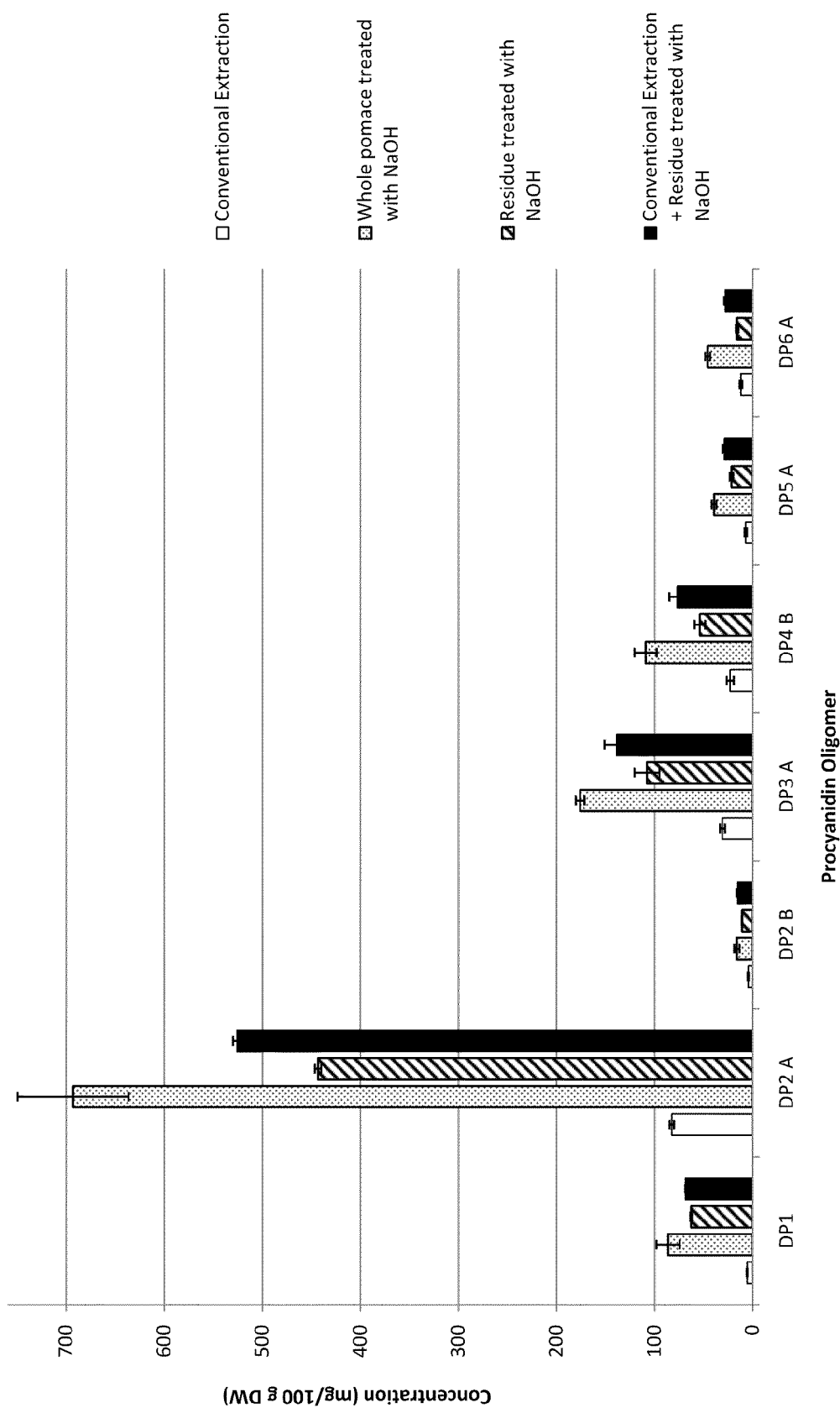
FIG. 4 is a graphical illustration of procyanidin oligomers (DP1-DP6) compositions of cranberry pomace before and after treatment with sodium hydroxide in accordance with an illustrative embodiment of the process of extracting procyanidins by alkaline hydrolysis disclosed herein, wherein treatment conditions were 2N sodium hydroxide at 60° C. for fifteen (15) minutes, and the residue was collected following conventional extraction by homogenization with acetone:water:acetic acid (70:29.5:0.5). "DPn A" indicates a procyanidin containing at least one A-type linkage, and "DPn B" indicates a procyanidin containing only B-type linkages.
Figure 5:
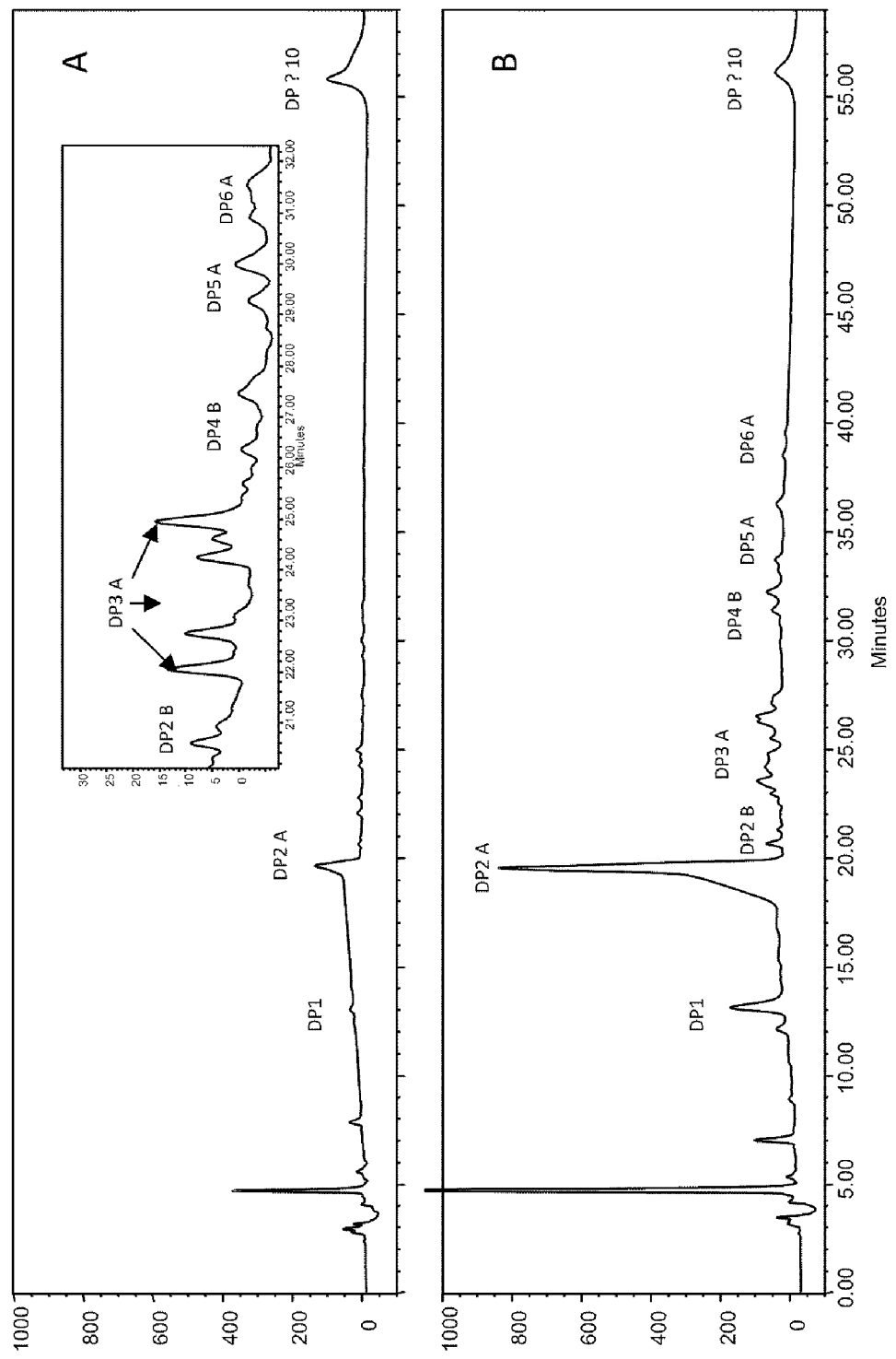
FIGS. 5A and 5B are HPLC chromatograms of procyanidins in cranberry pomace before (A) and after (B) treatment with sodium hydroxide, wherein treatment conditions were 2N sodium hydroxide at 60° C. for fifteen (15) minutes.

[a]Acetone/Water/Acetic Acid (70:29.5:0.5)
[b]Mean ± standard deviation (n = 3)
[c]Flavonols were quantified as myricetin or quercetin equivalents
[d]A-type procyanidins were quantified as corresponding B-type equivalents The amount of procyanidin oligomers further extracted from the residue after sodium hydroxide treatment is shown in FIG. 4. Treatment of the residue with sodium hydroxide resulted in further extraction of procyanidins that were not released by conventional solvent extraction, but the amount extracted was not as high as when whole cranberry pomace was treated with sodium hydroxide. When whole cranberry pomace was treated with sodium hydroxide, a total of 1166.1 mg/100 g DW procyanidin oligomers (DP1-DP6) were extracted. However, when the residue was treated with sodium hydroxide, and the procyanidins were extracted and added to the "free" procyanidins, only 882.1 mg/100 g DW were extracted. This is a 24% lower yield than when the whole pomace was treated with sodium hydroxide, but it is still significantly more than the amount of procyanidins extracted conventionally without treatment with sodium hydroxide (165.7 mg/100 g DW).

Treatment of cranberry pomace with sodium hydroxide effectively enhances the extraction of procyanidin monomers and oligomers, which is coupled with a significant loss in polymeric procyanidins. An increase in reaction temperature allows for enhanced extraction of DP1-DP3 procyanidins. Additionally, the time needed for procyanidins to be released is much lower at 60° C. for fifteen (15) minutes than at 25° C. for less than twenty-four (24) hours. Under harsher conditions (e.g., longer treatment times, higher temperatures), procyanidin yields were lower, indicating degradation. Procyanidins degraded in a pH dependent manner by alkaline treatment and are unstable at high temperatures.

Example 3

Figure 6:
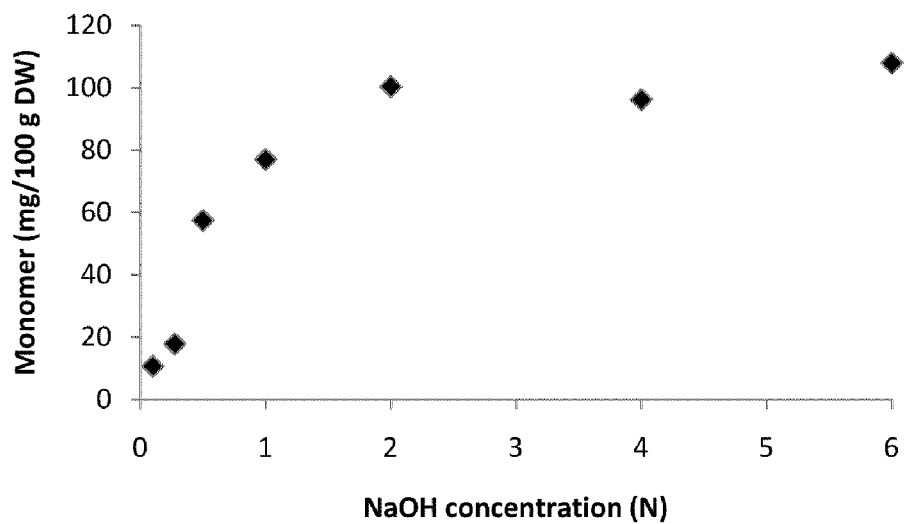
FIG. 6 is a graphical illustration of procyanidin monomer concentrations after alkaline hydrolysis of cranberry pomace with varying sodium hydroxide concentrations at 60° C. for fifteen (15) minutes in accordance with an illustrative embodiment of the process of extracting procyanidins by alkaline hydrolysis disclosed herein.
Figure 7:
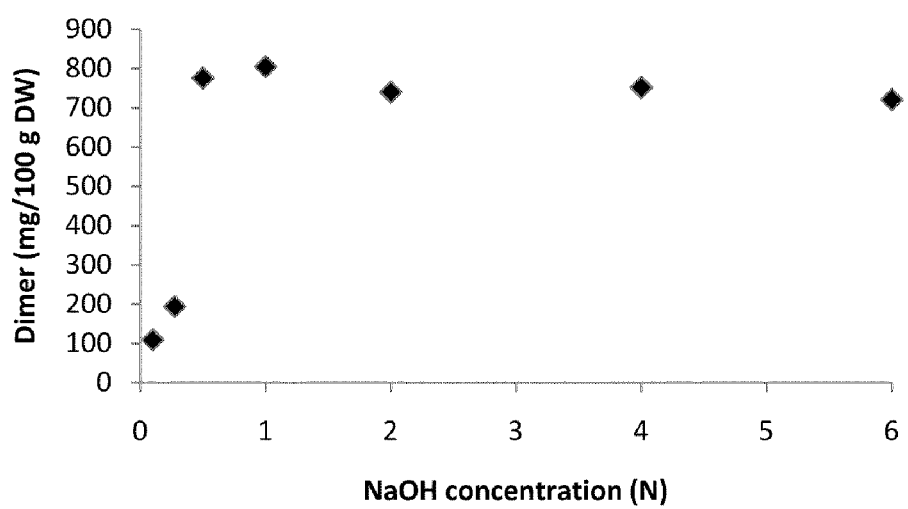
FIG. 7 is a graphical illustration of procyanidin dimer concentrations after alkaline hydrolysis of cranberry pomace with varying sodium hydroxide concentrations at 60° C. for fifteen (15) minutes in accordance with an illustrative embodiment of the process of extracting procyanidins by alkaline hydrolysis disclosed herein.

Cranberry pomace was treated with varying concentrations of sodium hydroxide at 60° C. for fifteen (15) minutes. Concentrations of sodium hydroxide included 0.1, 0.275, 0.5, 1.0, 2.0, 4.0, and 6.0N. As illustrated in FIG. 6, the amount of monomers extracted increased with increasing sodium hydroxide concentration up to 2N, at which point it began to level off. The amount of dimers extracted increased up to 0.5N and then leveled off, as shown in FIG. 7.

Example 4

Figure 8:
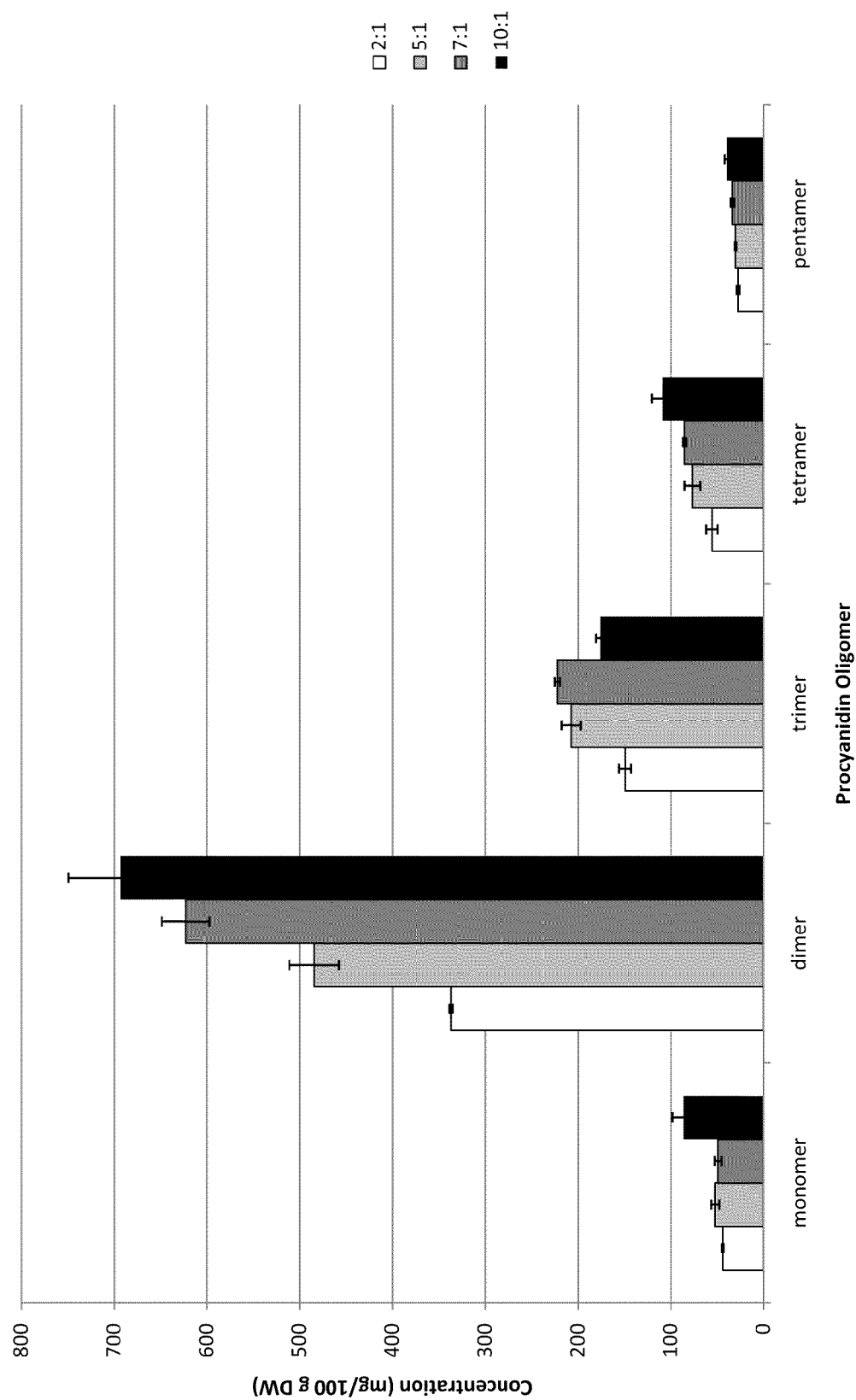
FIG. 8 is a graphical illustration of procyanidin oligomer concentration of cranberry pomace after alkaline hydrolysis using varying sodium hydroxide to pomace ratios in accordance with an illustrative embodiment of the process of extracting procyanidins by alkaline hydrolysis disclosed herein.

Cranberry pomace was treated with 2N sodium hydroxide at 60° C. for fifteen (15) minutes using varying sodium hydroxide:pomace ratios. As can be seen in FIG. 8, generally, ratios of 7:1 and 10:1 provided the greatest extraction of procyanidin oligomers.

Example 5

Blueberry and grape pomace and three varieties of wine grape seeds were treated with 2N sodium hydroxide for fifteen (15) minutes at 60° C. with shaking. As can be seen in Table 5, an increase in monomers and dimers occurred upon treatment of all samples compared to the conventional extraction. Procyanidin oligomers greater than dimers were generally degraded by alkaline hydrolysis.

TABLE 5

Procyanidins (mg/100 g DW) extracted from blueberry and grape pomace and grape seeds by conventional extraction and alkaline hydrolysis

| Sample | Conventional Extraction | | Alkaline Hydrolysis | | Increase[a] | |
|---|---|---|---|---|---|---|
| | Monomer | Dimer | Monomer | Dimer | Monomer | Dimer |
| Blueberry Pomace | 11.4 ± 2.4[b] | 75.4 ± 7.7 | 168.9 ± 16.1 | 1052.8 ± 23.1 | 14.8 | 14.0 |
| Sunbelt Grape Pomace | 374.9 ± 22.1 | 120.4 ± 0.4 | 514.8 ± 62.7 | 514.1 ± 68.6 | 1.4 | 4.3 |
| Merlot Grape Seeds | 163.6 ± 8.2 | 156.9 ± 1.5 | 494.4 ± 75.1 | 2109.1 ± 199.8 | 3.0 | 13.4 |
| Chardonnay Grape Seeds | 428.5 ± 109.3 | 158.1 ± 33.6 | 778.6 ± 65.8 | 2366.4 ± 225.9 | 1.8 | 15.0 |
| Riesling Grape Seeds | 577.4 ± 129.3 | 463.6 ± 50.8 | 883.3 ± 40.3 | 3527.3 ± 370.7 | 1.5 | 7.6 |

[a]Values equal to amount extracted by alkaline hydrolysis divided by amount extracted by conventional extraction
[b]Values represent means ± standard deviation (n = 3)

Example 6

Alkaline hydrolysis was performed using 2N potassium hydroxide instead of 2N sodium hydroxide. Pomace was treated with 2N potassium hydroxide at 60° C. for fifteen (15) minutes. This resulted in greater extraction compared to the conventional solvent extraction with 40.1, 447.5, and 164.5 mg/100 g DW of monomers, dimers, and trimers extracted, respectively. Calcium hydroxide was also evaluated; however, it was unable to be used due to its low solubility.

Extraction with ethyl acetate provides a process of fractionation of low DP procyanidins from high DP procyanidins and other phenolic compounds. Although aqueous acetone is known to be an effective solvent to extract procyanidins, the extracts require further purification steps to isolate procyanidins from other polyphenolics (e.g., anthocyanins, flavonols) prior to HPLC analysis. Ethyl acetate is an effective extraction solvent for low DP procyanidins. This process of extracting bound procyanidins could be useful in an industrial application where it might be desired to separate procyanidins based on their molecular weight.

Inhibition of Adherence of Uropathogenic *E. coli* by Cranberry Pomace Extracts Obtained Conventionally and by Alkaline Hydrolysis Cranberry pomace extracts were tested on their ability to prevent the adhesion of uropathogenic *E. coli* to human uroepithelial cells, and four (4) different extracts were tested for their anti-adherence activity. As can be seen in Table 6 supra, the first extract came from conventional extraction of cranberry pomace (100 mg). The remaining three (3) extracts were three (3) procyanidins fractions resulting from alkaline treated cranberry pomace (100 mg). The first extract was the ethyl acetate fraction, which contained only DP1-DP3 procyanidins, the second extract was the aqueous fraction, which contained procyanidins with DP$\geq$4, and the third extract contained all procyanidins extracted by alkaline hydrolysis. Weights presented in Table 6 indicate the total weight of procyanidins that was obtained in each extract from 100 mg of pomace, and percent anti-adherence values are based on 0.8 mg/mL of whole pomace.

As can be seen, anti-adherence was greatest in the fraction obtained from alkaline hydrolysis containing all procyanidins, which was more than twice as effective as procyanidins obtained by conventional extraction. This was followed by the alkaline hydrolysis fraction containing DP$\geq$4. The lowest percentage of anti-adherence was observed in the DP1-DP3 procyanidin fraction, indicating that higher oligomers, but not polymers, are more effective at preventing adhesion.

TABLE 6

Anti-adhesion Properties of Cranberry Pomace

| Sample | Amount of Total Procyanidins (mg)$^a$ | % Anti-adherence$^b$ |
|---|---|---|
| Untreated | 0.95 | 17.37 |
| Alkaline DP1-DP3 | 0.83 | 13.15 |
| Alkaline DP $\geq$ 4 | 0.80 | 31.19 |
| Alkaline All Procyanidins | 1.7 | 36.15 |

$^a$Procyanidins were obtained from 100 mg cranberry pomace
$^b$Percentage of anti-adherence based on 0.8 mg/mL of whole pomace In sum, the process of extracting bound procyanidins by alkaline hydrolysis results in an increase in procyanidin extraction, and greater amounts are extracted at higher temperature, short time combinations. As discussed above, the most procyanidins oligomers (DP1-DP3) are extracted at 60° C. for fifteen (15) minutes with each concentration of the alkali. When compared to conventional extraction using homogenization with solvent, the process of extracting bound procyanidins by alkaline hydrolysis increases procyanidin oligomers extraction by 3.8-fold to 14.9-fold, with the greatest increase being DP1 (14.9-fold) and A-type DP2 (8.4-fold) procyanidins. Treatment of the residue remaining after conventional solvent extraction with an alkali hydroxide compound, such as sodium or potassium hydroxide, under the process of extracting bound procyanidins by alkaline hydrolysis also results in increased procyanidin extraction.

Whereas, the processes have been described in relation to the drawings and claims, it should be understood that other and further modifications, apart from those shown or suggested herein, may be made within the spirit and scope of this invention.

What is claimed is:

1. A process of extracting procyanidins from a procyanidin-containing plant material, said process comprising the steps of:
    (a) treating said procyanidin-containing plant material with a hydroxide compound having a normality of approximately 0.1 to approximately 6.0 in the presence of an inert gas for approximately 15 minutes and at a temperature of approximately 60° C.;
    (b) subsequent to said step (a), neutralizing said hydroxide compound to a pH of approximately 2 to approximately 7;
    (c) subsequent to said step (b), extracting lipids;
    (d) subsequent to said step (c), extracting procyanidin monomers, dimers and trimers from said procyanidin-containing plant material using ethyl acetate; and
    (e) subsequent to said step (c), extracting procyanidin tetramers, pentamers and hexamers from said procyanidin-containing plant material by homogenization with acetone:water:acetic acid.

2. The process of claim 1 wherein said procyanidin-containing plant material is selected from the group consisting of cranberry pomace, apple pomace, pine bark, cinnamon, cocoa, grape seed, grape pomace, bilberry pomace, black currant pomace, green tea, black tea, chokeberry pomace, blueberry pomace and sorghum.

3. The process of claim 1 wherein said step (a) of treating said procyanidin-containing plant material with said hydroxide compound further comprises the step of treating said procyanidin-containing plant material with said hydroxide compound at a hydroxide:procyanidin-containing plant material ratio from approximately 2:1 to approximately 10:1.

4. The process of claim 1 wherein said hydroxide compound is sodium hydroxide or potassium hydroxide.

5. The process of claim 1 wherein said step (b) of neutralizing said hydroxide compound further comprises the step of adjusting the pH to approximately 2 to approximately 7 using an acid.

6. The process of claim 5 wherein said acid is concentrated hydrochloric acid having a normality of approximately 4.

7. The process of claim 1 wherein said step (c) of extracting lipids further comprising the step of extracting lipids by shaking with hexane.

8. The process of claim 1 wherein said step (d) of extracting said procyanidin monomers, dimers and trimers further comprises the step of fractionating and isolating said procyanidin monomers, dimers and trimers fractions from said procyanidin-containing plant material using ethyl acetate.

9. A process of extracting procyanidins from a procyanidin-containing pomace residue, said process comprising the steps of:
    (a) homogenizing a procyanidin-containing pomace and a solvent to form a pomace mixture;
    (b) subsequent to said step (a), extracting procyanidins monomers through polymers from said pomace mixture leaving said pomace residue;
    (c) subsequent to said step (b), removing any excess of said solvent from said pomace residue;
    (d) subsequent to said step (c), dissolving said pomace residue in an aqueous solution of a hydroxide compound;
    (e) subsequent to said step (d), heating said aqueous solution to a predetermined temperature for a predetermined amount of time;

(f) subsequent to said step (e), substantially neutralizing the pH of said aqueous solution using an acid; and (g) subsequent to said step (f), extracting said procyanidins from said pomace residue.

10. The process of claim 9 further comprising the step of cooling said aqueous solution subsequent to said step (e) of heating said aqueous solution and prior to said step (f) of substantially neutralizing the pH of said aqueous solution.

11. The process of claim 9 further comprising the step of separating lipids in said aqueous solution by shaking with hexane subsequent to said step (f) of substantially neutralizing the pH of said aqueous solution and prior to said step (g) of extracting said procyanidins.

12. The process of claim 9 wherein said step (d) of dissolving said pomace residue in said aqueous solution of said hydroxide compound is performed at a hydroxide:procyanidin-containing pomace residue ratio of approximately 2:1 to approximately 10:1.

13. The process of claim 9 wherein said hydroxide compound is sodium hydroxide or potassium hydroxide having a normality from approximately 0.1 to approximately 6.0.

14. The process of claim 9 wherein said step (f) of substantially neutralizing the pH of said aqueous solution further comprises adjusting the pH of said aqueous solution to a pH of between about 2 and about 7 using concentrated hydrochloric acid having a normality of approximately 4.

15. The process of claim 9 where said step (g) of extracting said procyanidins further comprises the steps of:

extracting procyanidin monomers, dimers and trimers from said pomace residue with ethyl acetate; and extracting procyanidin tetramers, pentamers and hexamers from said pomace residue by homogenization with acetone:water:acetic acid.

16. The process of claim 9 wherein said procyanidin-containing pomace is selected from the group consisting of cranberry pomace, apple pomace, pine bark, cinnamon, cocoa, grape seed, grape pomace, bilberry pomace, black currant pomace, green tea, black tea, chokeberry pomace, blueberry pomace and sorghum.

17. The process of claim 9 said step (e) further comprises heating said aqueous solution to a temperature of approximately 25° C. to approximately 60° C. for approximately 5 minutes to approximately 24 hours.

18. The process of claim 15 wherein said step of extracting said procyanidin monomers, dimers and trimers further comprises the step of fractionating and isolating said procyanidin monomers, dimers and trimers from said procyanidin-containing plant material using ethyl acetate.

* * * * *